United States Patent [19]

Turner et al.

[11] Patent Number: 4,983,516
[45] Date of Patent: Jan. 8, 1991

[54] BIOELECTROCHEMICAL MEASUREMENT OF MICROBIAL ACTIVITY USING A WORKING ELECTRODE OF CARBON-BEARING POROUS MATERIAL

[75] Inventors: Anthony P. F. Turner, Cranfield; Alan P. Hodges, Pershore; Ann Franklin, Cranfield; Graham Ramsay, Cranfield; Davina Steel, Cranfield, all of England

[73] Assignee: Paul De La Pena Limited, Worcestershire, England

[21] Appl. No.: 910,453

[22] Filed: Sep. 23, 1986

[30] Foreign Application Priority Data

Sep. 25, 1985 [GB] United Kingdom ............... 8523631

[51] Int. Cl.⁵ ........................... C12Q 1/04; C12M 1/42
[52] U.S. Cl. ........................................ 435/34; 435/29; 435/30; 435/39; 435/173; 435/243; 435/261; 435/291; 435/817; 422/101
[58] Field of Search ............... 435/29, 30, 34, 173, 435/243, 261, 284, 291, 817, 39; 422/101

[56] References Cited

U.S. PATENT DOCUMENTS 3,403,081 9/1968 Rohrback et al. ............... 435/29

FOREIGN PATENT DOCUMENTS

| 498905 | 3/1979 | Australia. |
| 047898 | 3/1982 | European Pat. Off.. |
| 078636 | 5/1983 | European Pat. Off.. |
| 109767 | 5/1984 | European Pat. Off.. |
| 125137 | 11/1984 | European Pat. Off.. |
| 127958 | 12/1984 | European Pat. Off.. |
| 167248 | 1/1986 | European Pat. Off.. |
| WO82/04264 | 12/1982 | PCT Int'l Appl.. |
| 1284952 | 8/1972 | United Kingdom. |
| 1314612 | 4/1973 | United Kingdom. |
| 2029026 | 3/1980 | United Kingdom ............ 435/29 |
| 2105750A | 12/1981 | United Kingdom. |
| 2131954 | 6/1984 | United Kingdom ............ 435/29 |
| 2161274A | 1/1986 | United Kingdom. |

OTHER PUBLICATIONS

*Agric. Biol. Chem.*, vol. 48, No. 8, 1984, pp. 1969–1976.
*Trends in Analytical Chemistry*, vol. 3, No. 9, 1984, pp. 223–229.

*Primary Examiner*—Esther M. Kepplinger
*Assistant Examiner*—Carol A. Spiegel
*Attorney, Agent, or Firm*—Larson and Taylor

[57] ABSTRACT

Microbial activity in an aqueous medium is measured in a bioelectrochemical cell in which the working electrode comprises an electrically conductive carbon-bearing porous material; suitably a graphitized carbon felt or cloth. This enhances the BEC response by increasing the surface area and by absorbing microbes onto the surface; and the electrode material can also be used to preconcentrate the microbes prior to use as an electrode in the cell.

7 Claims, 1 Drawing Sheet

BIOELECTROCHEMICAL MEASUREMENT OF MICROBIAL ACTIVITY USING A WORKING ELECTRODE OF CARBON-BEARING POROUS MATERIAL

This invention relates to the measurement of microbial activity by means of a bioelectrochemical cell (BEC).

The use of BEC for collecting data on microbial activity has been investigated by a number of workers in recent years: see for example AU 498905; WO 82/04264; Matsunaga et al, Appl. Environ. Microbial. 37, 117–121 (1979) and Eur. J. Appl. Microbiol. 10, 125–132 (1980); Turner et al Biotechnology and Bioengineering Symposium No. 12 (1982) 401–412; Turner et al, Biochemical Society Transactions, 11, 445–448 (1983). The accurate determination of microbial activity is of considerable interest in, for example the food and drink industry, water and environmental pollution control, clinical analysis, including antibiotic sensitivity under clinical applications, etc. The present invention is directed to improvements in BEC methods and equipment for monitoring microbial activity.

According to one aspect of the present invention there is provided a bioelectrochemical cell having a working electrode comprising an electrically conductive carbon-bearing porous material. The carbon is preferably in the form of graphite. The electrode preferably comprises graphitized carbon felt or cloth, but other materials could be used, for example solid porous compressed graphite.

In another aspect the present invention provides an electrically conductive carbon-bearing porous electrode for use in a bioelectrochemical cell.

In a third aspect of the present invention there is provided a method of measuring microbial activity in aqueous medium by means of a bioelectrochemical cell, characterized in that the bioelectrochemical cell has a working electrode of electrically conductive carbon-bearing porous material.

Other preferred and useful features of the invention will become apparent from the following description.

Figure 1:
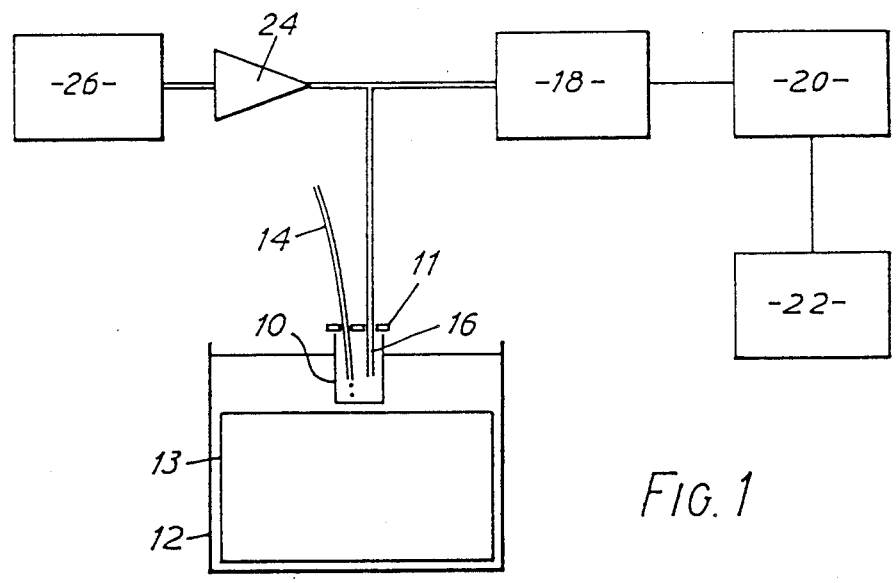
FIG. 1 shows a diagrammatic view of a BEC configuration for measuring microbial activity in an aqueous sample.

Referring to FIG. 1; the bioelectrochemical cell is contained in a beaker 10 with a lid 11, and placed in a water bath 12 with a magnetic stirrer 13. If desired, e.g. for the analysis of obligate anaerobes, nitrogen is bubbled into the cell from a nitrogen line 14. The electrodes, indicated generally at 16, comprise a platinum electrode and an Ag/AgCl reference electrode. The output from the electrodes is taken to suitable data processing equipment. As illustrated, this comprises: a low noise current-to-voltage converter 18, a low noise by-pass filter 20, a digital volt meter 22, a buffer 24 and a precision voltage reference 26.

Figures 2, 3, 4:
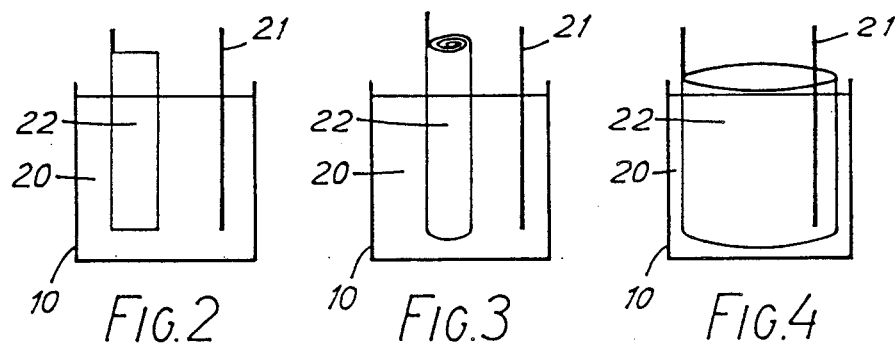
FIGS. 2 to 4 show diagrammatically various embodiments of BEC according to the present invention.

FIGS. 2 to 4 show different embodiments of the BEC according to the present invention which can be used with the configuration shown in FIG. 1. Each cell contains an aqueous analyte sample 20, an Ag/AgCl reference electrode 21 and a working electrode 22. The working electrode in each case is made from RVG 1000 grade of graphitized carbon felt, supplied by Le Carbone (Great Britain) Ltd., of Portslade, Sussex, BN4 2LX. The felt has the following properties:

| | |
|---|---|
| Electrical resistance | 1.7 ohms/cm$^2$ |
| Weight m$^{-2}$ | 150 g |
| Thickness | 1.2 mm |
| Carbon content | >99% |

In the embodiment shown in FIG. 2, the working electrode takes the form of a planar strip of the carbon felt or cloth. In the embodiment shown in FIG. 3, it takes the form of a cylindrical roll of the carbon felt or cloth. In the embodiment shown in FIG. 4 it takes the form of a large open cylinder of the carbon felt or cloth.

A direct comparison was carried out of the response obtained with these three configurations of BEC, and the response obtained from a normal BEC using a platinum working electrode. The results obtained are shown in Table 1. 100 µl (250 mM) of potassium ferricyanide were used in each cell as a mediator.

TABLE 1

Use of carbon felt or cloth as an alternative working electrode in the BEC

| Organism | Optical Density | Volume added (µl) | Working electrode | Maximum slope (µA min$^{-1}$) |
|---|---|---|---|---|
| E. coli | 0.44 | 500 | Platinum | 1.31 (control) |
| E. coli | 0.44 | 500 | Carbon cloth strip equivalent size | 5.03<br>2.6 |
| Yersinia enterocolitica | 0.85 | 1000 | Platinum | 2.1 (control) |
| Yersinia enterocolitica | 0.85 | 1000 | Carbon cloth strip equivalent size | 14.93<br>15.75 |
| E. coli | 0.44 | 500 | Platinum | 0.85<br>0.54 (control) |
| E. coli | 0.44 | 500 | Carbon cloth rolled up 3.5 × 4.5 cm | 12.98<br>16.55 |
| E. coli | 0.49 | 500 | Platinum | 0.98<br>1.04 (control) |
| E. coli | 0.49 | 500 | Carbon cloth rolled up 3.5 × 4.5 cm | 7.45<br>14.6 |

The results shown in Table 1 indicate that the slope measurement (electrical output) was enhanced significantly using a carbon cloth working electrode as compared with a platinum electrode, single sided of 7.5 cm$^2$ area. For example, for a strip of carbon cloth of equivalent dimensions to the platinum working electrode, the maximum slope values were increased 5- to 7- fold. For a rolled up carbon cloth electrode of dimensions 3.5×4.5 cm, the maximum slope values were increased 10- to 20-fold.

Experiments were also carried out to investigate the effect on the electrical response of increasing the surface area of the working electrode. The control BEC contained ferricyanide mediator (500 µl, 250 mM) with 150 µl E. coli (O.D. 1.7). The results which appear in Table 2 show that enhancement of the E. coli BEC response relative to that obtained with standard platinum/silver chloride paired electrodes (0.5×1.5 cm) increased with increasing area of the working electrode. The largest enhancement was obtained with the 12.5 cm$^2$ cylindrical electrode, which was the largest electrode that could be fitted into the 10 ml beaker used.

TABLE 2

| Area of RVG 1000 electrode (cm$^2$) | Enhancement of maximum slope |
|---|---|
| Planar 0.75 (same surface area as platinum working electrode) | None |
| Planar 3.0 | 2.5 (n = 2) |
| Roll 6.0 | 8.1 (n = 1) |
| Cylindrical 7.5 | 10.9 (n = 3) |
| Cylindrical 12.5 | 19.3 (n = 3) |

As a negative control, RVG 1000 cloth cylindrical electrode (area 12.5 cm$^2$) with 0.1% peptone water (500 µl) produced no response in the BEC.

DETECTION OF LOW CONCENTRATIONS OF E. COLI IN THE BEC

The working electrode was made from RVG 1000 carbon felt or platinum foil. The platinum foil working electrode was in the standard configuration, that is mounted on a plastic support on the opposite side to an Ag/AgCl reference electrode. The carbon cloth electrode was one of two shapes. It was either a cylinder of rolled-up cloth, of initial dimensions 4.5 cm×3.5 cm (height×width), or an open cylinder of height 3.0 cm and outside diameter 2.3 cm. In the former case the reference electrode was a standard single sided Ag/AgCl reference electrode (0.5 cm×1.5 cm). In the latter configuration the reference electrode was a cylinder of AgCl coated silver foil (diameter: 0.95 cm, height: 2.00 cm). 10 standard BEC electrolyte (150 µl of potassium ferricyanide, 250 mM) was used with the platinum working electrode. When the large (12.5 cm$^2$) carbon cloth electrodes were used, the total electrolyte volume was 8.0 ml. The electrolyte consisted of sodium phosphate buffer (6.4 ml, pH 7.0, 50 mM), potassium chloride (0.8 ml, 1.0 M), potassium ferricyanide (150 µl, 250 mM), glucose (150 µl, 25 mM) and E. coli cells (0.5 ml). All BEC experiments were carried out at 39.5° C. The E. coli was harvested in the stationary phase, after overnight growth on nutrient broth in a 250 ml shake flask (150 rpm, 30° C.).

The results of these experiments are presented in Table 3.

TABLE 3

| | | Detection of low concentrations of E. coli | | | | |
|---|---|---|---|---|---|---|
| E. coli BEC concentration (cells ml$^{-1}$) | Working electrode material | Working electrode shape | Working electrode area (cm$^2$) | Maximum slope (µA min$^{-1}$) | Maximum current (µA) | Total electrolyte volume (ml) |
| 1.1 × 10$^6$ | Carbon RVG 1000 | Closed cylinder | 6.5 | 1.2 (n = 4) | 2.4 (n = 4) | 10.0 |
| 1.1 × 10$^6$ | Platinum | Planar | 0.7 | Not measured | 0.2 (n = 2) | 10.0 |
| 1.4 × 10$^6$ | Carbon RVG 1000 | Open cylinder | 12.5 | 15.9 (n = 1) | 4.5 (n = 2) | 8.0 |
| 1.4 × 10$^6$ | Carbon RVG 1000 | Closed cylinder | 5.2 | >30 (n = 2) | 5.8 (n = 2) | 8.0 | n = number of replicate experiments

The lowest concentration of E. coli that was tested was 1.1 ×10$^6$ cells ml$^{-1}$. The carbon cloth electrode (6.5 cm$^2$) gave a maximum current (2.4 µA) that was twelve times that of the platinum electrode (0.7 cm$^2$). The signal to noise ratios obtained using carbon cloth ranged from 2.8 to 21.4. Hence it should be feasible to detect less than 10$^6$ cells ml$^{-1}$. When a larger carbon cloth electrode was used there was no significant change in the maximum current.

USE OF CARBON FELT OR CLOTH AS PRE-CONCENTRATION MEDIUM

The effectiveness of carbon felt or cloth as a bacterial filter was investigated as follows:

Strips of RVG1000 carbon felt were rolled into spirals and inserted into the bore of a graduated 10 ml pipette (i.d. 8 mm). Known volumes of aqueous suspensions of bacteria (prepared from mixed cultures obtained from real samples of used cutting fluids) were transferred to the pipette and allowed to fall, by gravity, through the spiral plug of carbon felt. The concentrations of bacteria in the original sample and in the filtrate were determined immediately before and after each experiment by standard plate count. The total number of bacterial cells in each sample was calculated from the concentration measurement and the number of bacteria retained in the felt plug was obtained by difference. This was expressed as a proportion of the total number in each sample (% retention) and as a concentration since the volume of liquid in the plug was known.

Results are given in Table 4:

TABLE 4

| SAMPLE NUMBER | CARBON FELT | | SAMPLE | | | FILTRATE | | |
|---|---|---|---|---|---|---|---|---|
| | AREA | VOLUME | VOLUME | CONC./ML | TOTAL | VOLUME | CONC./ML | TOTAL |
| 1 | 37 × 65 mm | 1.8 ml | 50 ml | 6.4 × 10$^7$ | 3200 × 10$^6$ | 48 ml | 5.35 × 10$^6$ | 256 × 10$^6$ |
| 2 | 29 × 65 mm | 1.4 ml | 50 ml | 1.39 × 10$^7$ | 695 × 10$^6$ | 48 ml | 9.45 × 10$^6$ | 459 × 10$^6$ |
| 3 | 37 × 65 mm | 1.8 ml | 20 ml | 1.35 × 10$^7$ | 270 × 10$^6$ | 18 ml | 6.8 × 10$^6$ | 122 × 10$^6$ |
| 4 | 37 × 65 mm | 1.8 ml | 100 ml | 1.97 × 10$^7$ | 1970 × 10$^6$ | 98 ml | 1.11 × 10$^7$ | 1088 × 10$^6$ |
| 5 | 29 × 65 mm | 1.4 ml | 50 ml | 1.14 × 10$^5$ | 5.7 × 10$^6$ | 48 ml | 1.02 × 10$^5$ | 4.89 × 10$^6$ |

| SAMPLE NUMBER | SAMPLE TOTAL | CARBON FELT % RETENTION | CARBON FELT CONC./ML, | CONC. FACTOR |
|---|---|---|---|---|

TABLE 4-continued

|   |                  |    |                   |           |
|---|------------------|----|-------------------|-----------|
| 1 | 2944 × 10⁶       | 92 | 1.63 × 10⁹        | 25 (27.8) |
| 2 | 236 × 10⁶        | 34 | 1.68 × 10⁸        | 12 (35.7) |
| 3 | 148 × 10⁶        | 55 | 8.2 × 10⁷         | 6 (11.1)  |
| 4 | 882 × 10⁶        | 45 | 4.9 × 10⁸         | 25 (55.5) |
| 5 | 8.1 × 10⁵        | 14 | 5.8 × 10⁵         | 5 (35.7)  |

THE USE OF A FILTER/ELECTRODE TO INCREASE THE BEC RESPONSE OF *PSEUDOMONAS AERUGINOSA*

Figure 5:
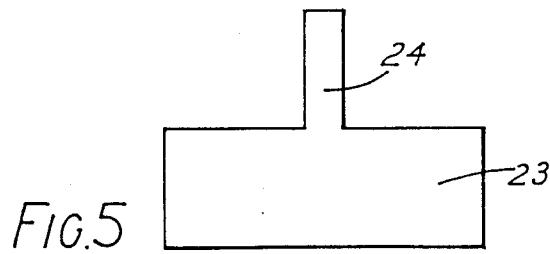
FIG. 5 shows a blank of a graphite cloth for forming an electrode.

FIG. 5 shows the configuration of a graphite cloth used to make a filter electrode. The graphite cloth (Le Carbone: TGM 285) had a geometric working area of 17.5 cm$^2$. It comprised a rectangular body portion 23 measuring 7.0×2.5 cm, and a contact strip portion 24 measuring 2.5×0.5 cm.

To form a filter the electrode was tightly rolled up with the contact strip inside the roll and pushed inside a syringe (Sabre:2 ml:internal diameter ca. 9 mm). The end of the syringe had been removed to allow the filter/electrode to be pushed out of the syringe barrel with the plunger.

The filtration efficiency was determined by repeatedly passing the same sample of *P. aeruginosa* through the filter and measuring the optical density (O.D.$_{600}$) of the filtrate. The final volume of the filtrate was measured. The results are shown in Table 5.

TABLE 5

| Number of filtration passes | O.D.$_{600}$ |
|---|---|
| 0 | 1.02 |
| 1 | 0.31 |
| 2 | 0.19 |
| 3 | 0.16 |
| 4 | 0.16 |
| 5 | 0.10 |
| 6 | 0.14 |

The sample was 2.0 ml of *Pseudomonas aeruginosa* (5×10$^9$ cells ml$^{-1}$).

The optical density of the filtrate decreased rapidly with the number of filtration passes and stabilised after three passes, possibly due to saturation of the filter. After six passes through the filter 93.5% of the bacteria remained on the filter.

To examine the use of the filter/electrode as a filter and as a working electrode, samples of a *P. aeruginosa* suspension (4 ml or 8 ml) or of a FAM2 blank (4 ml or 8 ml) were passed through the filter. The filter/electrode was ejected from the barrel of the syringe, unrolled and placed around the internal wall of the BEC. Platinum foil was folded around the ends of the contact strip of the working electrode to prevent wetting of the crocodile clip connectors with electrolyte that had seeped up the strip. The cell was assembled with an Ag/AgCl reference electrode that was single sided and had a geometric area of 0.75 cm$^2$. The electrolyte was sodium phosphate buffer (8.35 ml, pH 7.0, 50 mM) in potassium chloride solution (100 mM), glucose (150 μl, 25 mM), 1,4-benzoquinone (250 μl, 25 mM) and ferricyanide (250 μl, 250 mM). The experiments were carried out at 22° C. The results are shown in Table 6.

TABLE 6

| Sample | Sample vol. (ml) | Max. slope (μA min$^{-1}$) | Max. current (μA) |
|---|---|---|---|
| P. aeruginosa | 4.0 | 159 | 58 |
| FAM2 control | 4.0 | 37 | 18 |

TABLE 6-continued

| Sample | Sample vol. (ml) | Max. slope (μA min$^{-1}$) | Max. current (μA) |
|---|---|---|---|
| P. aeruginosa | 8.0 | ca. 700 | 136 |
| FAM2 control | 8.0 | 21 | 16 |

The concentration of the *P. aeruginosa* was 2×10$^8$ cells ml$^{-1}$.

These data demonstrated that both the maximum slope and the maximum current increased on doubling the volume of the bacterial suspension that was passed through the filter/electrode. The accuracy of the measurement of the maximum current was considerably higher than that of the manually measured maximum slopes. The doubling of the sample volume resulted in an increase of the signal to noise ratio of the maximum current from 3.3 to 8.4. The maximum current therefore approximately doubled as the sample volume was doubled. This demonstrated that a filter/electrode can enhance the BEC signal from a sample of *P. aeruqinosa*.

The results of the experiments described above show:
(i) that increasing the length of the carbon felt plug (given by the volume) raises the efficiency of the separation i.e. % retention values obtained with 1.8 ml are consistently higher than when using 1.4 ml,
(ii) that reasonable efficiency and repeatability is obtained independent of the starting volume of sample especially at the higher path length,
(iii) that concentration factors in excess of half the theoretical maximum can be achieved with relative ease.

It was concluded that carbon felt could be used verY satisfactorily to collect bacteria from a relatively large volume of aqueous suspension and to retain them in a relatively small volume thereby increasing the concentration of bacteria in the fluid. Carbon felt or cloth can therefore be shown to have three modes of action within the BEC:

(a) as an electrode, enhancing the BEC response by increasing the surface area,
(b) as an electrode, enhancing the BEC response due to adsorption of bacterial cells from the sample onto the carbon. This can be deduced from the results in Table 1, in particular the increase in maximum slope measured when *Yersinia enterocolitica* were examined in the BEC. The enhancement is clearly more than can be explained by a simple increase in surface area of the electrode,
(c) as a filter for preconcentrating bacteria prior to being used as an electrode as above.

The electrode conveniently uses graphitized carbon felt or cloth, but other materials could be used which combine porosity with active electrically conductive carbon of high surface area.

We claim:

1. A method of measuring microbial activity in an aqueous medium by means of a bioelectrochemical cell, wherein the cell has a working electrode comprising electrically conductive carbon-bearing porous material, said material being such as to permit filtration and retention of bacteria from an aqueous suspension thereof bacteria to be filtered through it, said method comprising contacting the working electrode with an aqueous medium whose microbial activity is to be measured and measuring an electrical response from the bioelectrochemical cell, the response being related to the microbial activity of said sample.

2. A method according to claim 1 wherein the carbon of said working electrode is in the form of graphite.

3. A method according to claim 2 wherein said working electrode comprises a graphitized carbon felt or cloth.

4. A method according to claim 1 wherein the measurement using the cell is preceded by passing a known volume of the aqueous medium through the porous electrode to preconcentrate bacteria in microbes on the electrode.

5. A method according to claim 4 wherein the electrode comprises a graphitized carbon felt or cloth, the felt or cloth having a body portion rollable into a spiral and a contact strip portion for connecting said electrode to an electrical connection.

6. A method according to claim 1 wherein the aqueous medium comprises a mediator for mediating electron transfer between said microbes and the working electrode.

7. A method according to claim 6 wherein the electrode comprises a graphitized carbon felt or cloth rolled into a spiral.

* * * * *